United States Patent [19]

d'Ostrowick et al.

[11] 3,969,421

[45] July 13, 1976

[54] PROCESS FOR PRODUCING ETHYLPHENOLS

[75] Inventors: Pierre Marie Joseph Ghislain de Radzitzky d'Ostrowick, Woluwe-St.-Lambert; Philippe Jean André Camerman, Wezembeek-Oppem, both of Belgium

[73] Assignee: Labofina S.A., Brussels, Belgium

[22] Filed: Feb. 10, 1975

[21] Appl. No.: 548,447

[30] Foreign Application Priority Data

Feb. 21, 1974 Belgium .............................. 141219

[52] U.S. Cl. ........................ 260/621 C; 260/624 R; 260/610 B
[51] Int. Cl.² ......................................... C07C 39/06
[58] Field of Search ......... 260/621 C, 610 B, 624 R

[56] References Cited
UNITED STATES PATENTS

| | | | |
|---|---|---|---|
| 2,661,375 | 12/1953 | Conner | 260/621 |
| 2,671,809 | 3/1954 | Fortuin et al. | 260/621 |

Primary Examiner—James O. Thomas, Jr.
Assistant Examiner—W. B. Lone

[57] ABSTRACT

A process for producing ethylphenol comprising reacting in liquid phase, diethylbenzene with a molecular oxygen containing gas, at a temperature between 100° and 180°C, until 5 to 30% of the diethylbenzene feed is converted into diethylbenzene hydroperoxide, withdrawing the reaction mixture, evaporating the unconverted diethylbenzene therefrom to obtain a concentrate containing at least 40% of diethylbenzene hydroperoxide, and recycling the unconverted diethylbenzene to the oxidation stage, mixing the diethylbenzene hydroperoxide concentrate with a solvent selected from the group consisting of low molecular weight aliphatic alcohols, ketones and mixtures thereof, decomposing said hydroperoxide by intimate contact with a strong acid which is used in an amount of between 0.05 and 5% of the weight of total reaction mixture, neutralizing the resulting mixture and thereafter distilling the neutralized mixture to recover a bottom fraction containing ethylphenol and an overhead fraction containing acetaldehyde, and treating said ethylphenol fraction with a compound reactive to the ketones within said fraction and thereafter distilling such treated fraction to obtain ethylphenol substantially free of ketonic impurities.

7 Claims, No Drawings

PROCESS FOR PRODUCING ETHYLPHENOLS

BACKGROUND OF THE INVENTION

The present invention relates to a process for producing ethylphenols and acetaldehyde. More particularly, the present invention relates to a process for producing ethylphenols with a high degree of purity.

Copending U.S. Patent application Ser. No. 334,084 filed Feb. 20, 1973, now U.S. Pat. No. 3,923,909 describes a process for producing ethylphenols and acetaldehyde which comprises reacting in liquid phase, diethylbenzene with a molecular oxygen containing gas, at a temperature between 100° and 180°C, until 5 to 30% of the diethylbenzene feed is converted into diethylbenzene hydroperoxide, withdrawing the reaction mixture, evaporating the unconverted diethylbenzene therefrom to obtain a concentrate containing at least 40% of diethylbenzene hydroperoxide, and recycling the unconverted diethylbenzene to the oxidation stage, mixing the diethylbenzene hydroperoxide concentrate with a solvent selected from the group consisting of low molecular weight aliphatic alcohols, ketones and mixtures thereof, decomposing said hydroperoxide by intimate contact with a strong acid which is used in an amount of between 0.05 and 5% of the weight of total reaction mixture, neutralizing the resulting mixture and thereafter distilling the neutralized mixture to recover a bottom fraction containing ethylphenol and an overhead fraction containing acetaldehyde. In certain applications, for example as precursors for phosphates used as plasticizers of vinyl chloride polymers, it is necessary that ethylphenol has a high degree of purity and particularly that it not be contaminated by aromatic ketones such as ethylacetophenone, acetophenone and propiophenone.

It is an object of the present invention to provide a new and improved process for the production of high purity ethylphenol.

Another object of the present invention is to provide a new and improved process for the production of ethylphenol substantially free of ketonic impurities.

A remaining object of the present invention is to provide a new and improved process for the purification of ethylphenol contaminated with ketonic impurities.

Additional objects will become apparent from the following description of the invention herein disclosed.

SUMMARY OF THE INVENTION

The present invention is a process for producing ethylphenol substantially free of ketonic impurities comprising reacting in liquid phase, diethylbenzene with a molecular oxygen containing gas, at a temperature between 100° and 180°C, until 5 to 30% of the diethylbenzene feed is converted into diethylbenzene hydroperoxide, withdrawing the reaction mixture, evaporating the unconverted diethylbenzene therefrom to obtain a concentrate containing at least 40% of diethylbenzene hydroperoxide, and recycling the unconverted diethylbenzene to the oxidation stage, mixing the diethylbenzene hydroperoxide concentrate with a solvent selected from the group consisting of low molecular weight aliphatic alcohols, ketones and mixtures thereof, decomposing said hydroperoxide by intimate contact with a strong acid which is used in an amount of between 0.05 and 5% of the weight of total reaction mixture, neutralizing the resulting mixture and thereafter distilling the neutralized mixture to recover a bottom fraction containing ethylphenol and an overhead fraction containing acetaldehyde, and treating said ethylphenol fraction with a compound reactive to the ketones within said fraction and thereafter distilling such treated fraction to obtain ethylphenol free of ketonic impurities.

According to the process described in the above referred to U.S. Pat. No. 3,923,909, the bottom fraction containing ethylphenol may be subjected either to a fractional distillation giving an overhead fraction of diethylbenzene and a heart fraction containing ethylphenol, or to an alkaline extraction which is followed by a wash of the extract with heptane, a regeneration of ethylphenol with sulfuric acid and a flash distillation. The process of the present invention may be applied for producing high purity ethylphenol whether the ethylphenol fraction has been subjected to either one of these treatments, or may be applied to the bottom fraction containing ethylphenol.

A preferred embodiment of the present invention comprises treating the bottom fraction with a compound reactive with ketones, eliminating water formed by the reaction, and thereafter distilling under reduced pressure in order to recover pure ethylphenol.

Another embodiment of the present invention comprises treating ethylphenol obtained after fractionated distillation or after alkaline extraction, as described in the above referred to U.S. Pat. No. 3,923,909 with the compound reactive with ketones, and thereafter subjecting to the fraction a further fractional distillation.

The compounds reactive with the ketones may be selected from the group consisting of hydrazine, hydrazine hydrate, the substitution derivatives of hydrazine such as phenylhydrazine, aminoguanidine and its substitution derivatives, hydroxylamine, semicarbazide and thiosemicarbazide and their substitution derivatives, particularly 4-aryl-semicarbazide and 4-aryl-thiosemicarbazide. Salts of hydroxylamine, of semicarbazides and of thiosemicarbazides also may be used. However, in such case, it is preferred to use a third solvent, such as methanol or ethanol. The choice of the compound reactive with the ketone depends on the price and availability and for that reason, hydrazine or hydrazine hydrate are most often used.

Ethylphenol obtained by the process described and claimed in the above referred to application Ser. No. 334,084 contains impurities which consist primarily of ketonic components and particularly of ethylacetophenone $C_2H_5.C_6H_4.COCH_3$. By reacting with the compounds reactive with the ketones, these ketonic impurities are converted into components having a higher boiling point, which are more easily separated from pure ethylphenol. If hydrazine hydrate is used, these impurities form hydrazones or cetazines according to the following reactions:

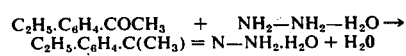

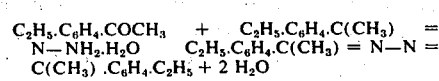

The compounds reactive with the ketones react with ethylphenol impurities and the reaction is carried out at a temperature generally between about 10° and 100°C. Higher temperatures may be applied if desired but without advantage. The reaction may be carried out at subatmospheric, atmospheric or superatmospheric pressures. The ketone reactive compound is used in sufficient amount to react with all of the ketonic impurities in the ethylphenol fraction. Therefore, the ketone reactive compound is used in an amount such that there is at least one —$NH_2$ reaction group of the ketone reactive compound per ketonic group in the impurities to be eliminated. When a ketone reactive compound with only one —$NH_2$ group is used, such as phenylhydrazine or hydroxylamine, this reactive is used in a molar ratio to the ketonic impurities of at least 1 : 1. With ketone reactive compounds containing two —$NH_2$ groups, for example with hydrazine, the molar ratio to the ketonic impurities is at least 0.5 : 1. An excess of ketone reactive compound may be used. In other words, the ketone reactive compound may be used in such an amount that the molar ratio to the ketonic impurities is higher than the above values and reaches for example 3 to 6, these compounds being easily separated from ethylphenol by distillation.

After treatment with the compound reactive with the ketone, ethylphenol is recovered in substantially pure form by distillation. In the overhead fraction, water produced by the condensation reaction of the ketones with the compound reactive therewith, is eliminated together with the third solvent and the excess of ketone reactive compound, if its boiling point is lower than that of ethylphenol.

The following examples are used to illustrate the invention and are not intended to limit it in any way.

EXAMPLE 1

Seventy-five and four tenths (75.4) grams m-ethylphenol having the composition given hereafter and containing 3.2 millimoles of ethylacetophenone were treated with 0.16 grams (3.2 millimoles) of hydrazine hydrate at atmospheric pressure and at a temperature of 100°C for a period of 20 minutes. The mixture was distilled under a reduced pressure of 40 mm Hg in order to obtain reaction water in the overhead fraction; thereafter, at a temperature of 127° – 129°C, ethylphenol was recovered (with a yield higher than 99%). The ethylphenol composition both before and after treating are given in the following table:

|  | m-ethylphenol untreated (% by weight) | m-ethylphenol treated and distilled (% by weight) |
|---|---|---|
| diethylbenzene | 0.010 | 0.002 |
| acetophenone | traces | — |
| m-ethylacetophenone | 0.630 | — |
| m-(ethylphenyl)carbinol | 0.009 | 0.009 |
| o-ethylphenol | 0.002 | traces |
| other impurities (undetermined) | 0.034 | 0.034 |
| m-ethylphenol | 99.315 | 99.955 |

EXAMPLE 2

One hundred (100) grams of 99.315% purity, having the same composition as in Example 1 above, were treated with 1.27 grams of 4-phenyl-semicarbazide, in a molar ratio of semicarbazide to ketone of 2 : 1. The mixture was then distilled as described in Example 1, but under 10 mm Hg M-ethylphenol was obtained at a temperature of 99°–100°C with a purity of 99.953%.

EXAMPLE 3

In the presence of 20 ml methanol, 100 g m-ethylphenol of 99.315% purity having the same composition as in Example 1, were treated with 0.29 gram hydroxylamine chlorohydrate, in an equimolar ratio to ethylacetophenone. The mixture was then distilled as described in Example 1. Water and methanol were eliminated in the overhead fraction and m-ethylphenol was obtained with 99.961% of purity.

What is claimed is:

1. In a process for producing ethylphenol comprising the steps of reacting in liquid phase, diethylbenzene with a molecular oxygen containing gas, at a temperature between 100° and 180°C, until 5 to 30% of the diethylbenzene feed is converted into diethylbenzene hydroperoxide, withdrawing the reaction mixture, evaporating the unconverted diethylbenzene therefrom to obtain a concentrate containing at least 40% of diethylbenzene hydroperoxide, and recycling the unconverted diethylbenzene to the oxidation stage, mixing the diethylbenzene hydroperoxide concentrate with a solvent selected from the group consisting of lower alkanols, lower alkanones and mixtures thereof, decomposing said hydroperoxide by intimately contacting the mixture of diethylbenzene hydroperoxide and solvent with a strong acid which is used in an amount of between 0.05 and 5% of the weight of total reaction mixture, neutralizing the resulting mixture and thereafter distilling the neutralized mixture to recover a bottom fraction containing ethylphenol and an overhead fraction containing acetaldehyde, the improvement which comprises the further steps of treating said ethylphenol fraction with a compound reactive to the ketones within said fraction, said compound being selected from the group consisting of hydrazine, hydrazine hydrate, the substitution derivatives of hydrazine, aminoguanidine, the substitution derivatives of aminoguanidine, hydroxylamine, semicarbazide, 4-aryl-semicarbazides, thiosemicarbazides, 4-aryl-thiosemicarbazides, and mixtures thereof and thereafter distilling such treated fraction to obtain ethylphenol substantially free of ketonic impurities.

2. The process of claim 1 wherein said ethylphenol fraction is treated at a temperature of between 10° and 100°C.

3. The process of claim 1 wherein the amount of said compound reactive with the ketones is such that there is at least one reaction group —$NH_2$ of such compound per ketonic group in the ketone impurities of the ethylphenol fraction.

4. The process of claim 3 wherein said compound reactive with the ketone is hydrazine.

5. The process of claim 3 wherein said compound reactive with the ketone is hydrazine hydrate.

6. The process of claim 4 wherein said hydrazine is employed in a molar ratio to ketonic impurities in said ethylphenol fraction of at least 0.5 : 1.

7. The process of claim 5 wherein said hydrazine hydrate is employed in a molar ratio to ketonic impurities in said ethylphenol fraction of at least 0.5 : 1.

* * * * *